(12) United States Patent
Shippy, III et al.

(10) Patent No.: US 7,691,082 B2
(45) Date of Patent: Apr. 6, 2010

(54) MEDICAL DEVICES

(75) Inventors: James Lee Shippy, III, Roswell, GA (US); Thomas J. Holman, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1215 days.

(21) Appl. No.: 11/174,258

(22) Filed: Jul. 1, 2005

(65) Prior Publication Data
US 2007/0016278 A1 Jan. 18, 2007

(51) Int. Cl.
*A61M 31/00* (2006.01)
(52) U.S. Cl. ............... 604/103.08; 604/103.06
(58) Field of Classification Search ......... 604/22, 604/103.08, 103.06, 103.07; 623/1.11
See application file for complete search history.

(56) References Cited

U.S. PATENT DOCUMENTS

| | | | |
|---|---|---|---|
| 3,752,617 A | | 8/1973 | Burlis et al. |
| 4,963,313 A | | 10/1990 | Noddin et al. |
| 5,087,246 A | | 2/1992 | Smith |
| 5,195,969 A | | 3/1993 | Wang et al. |
| 5,196,024 A | | 3/1993 | Barath |
| 5,209,799 A | | 5/1993 | Vigil |
| 5,270,086 A | | 12/1993 | Hamlin |
| 5,318,587 A | | 6/1994 | Davey |
| 5,336,234 A | | 8/1994 | Vigil et al. |
| 5,409,458 A | | 4/1995 | Khairkhahan et al. |
| 5,545,132 A | * | 8/1996 | Fagan et al. ............ 604/103.08 |
| 5,693,014 A | * | 12/1997 | Abele et al. ............ 604/103.08 |
| 5,714,110 A | | 2/1998 | Wang et al. |
| 5,826,588 A | * | 10/1998 | Forman ............ 128/898 |
| 6,129,706 A | | 10/2000 | Janacek |
| 6,132,824 A | * | 10/2000 | Hamlin ............ 428/35.2 |
| 6,210,364 B1 | | 4/2001 | Anderson et al. |
| 6,478,807 B1 | | 11/2002 | Foreman et al. |
| 6,482,348 B1 | | 11/2002 | Wang et al. |
| 6,517,888 B1 | | 2/2003 | Weber |
| 6,802,849 B2 | | 10/2004 | Blaeser et al. |
| 6,946,092 B1 | | 9/2005 | Bertolino et al. |
| 2002/0165523 A1 | | 11/2002 | Chin et al. |
| 2003/0163148 A1 | | 8/2003 | Wang et al. |
| 2004/0078052 A1 | | 4/2004 | St. Pierre et al. |

(Continued)

FOREIGN PATENT DOCUMENTS

WO  WO 01/32398  5/2001

OTHER PUBLICATIONS

U.S. Appl. No. 11/060,151, filed Feb. 17, 2005, Klisch et al.

*Primary Examiner*—Nicholas D Lucchesi
*Assistant Examiner*—Victoria P Campbell
(74) *Attorney, Agent, or Firm*—Crompton, Seager & Tufte, LLC

(57) ABSTRACT

Medical devices, for example, those that have balloons, and methods of making the devices are described. For example, in some embodiments, a medical device includes an elongated shaft, and an inflatable balloon carried by the shaft. The balloon includes a first recessed channel, a second recessed channel, a third recessed channel, and a fourth recessed channel, wherein the first recessed channel is spaced from the second recessed channel by a first distance, the third recessed channel is spaced from the fourth recessed channel by the first distance, and the second recessed channel is spaced from the third recessed channel by a second distance different than the first distance.

14 Claims, 8 Drawing Sheets

U.S. PATENT DOCUMENTS

2004/0133223 A1 7/2004 Weber
2005/0043679 A1 2/2005 Devens, Jr. et al.
2005/0043712 A1 2/2005 Devens, Jr.
2006/0182873 A1* 8/2006 Klisch et al. .................. 427/2.1

* cited by examiner

MEDICAL DEVICES

TECHNICAL FIELD

The invention relates to medical devices, such as those that include medical balloons, and methods of making the devices.

BACKGROUND

Medical devices that include balloons, such as balloon catheters, can be used to administer a variety of treatments. For example, in an angioplasty procedure, a balloon carried by a catheter can be used to widen a constricted bodily vessel, such as a coronary artery. A balloon catheter can also be used to deliver a tubular member, such as a stent, that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an acceptable rate of blood flow. After use, the balloon is collapsed and withdrawn.

In stent delivery, the stent is compacted on the balloon and transported to a target site. Upon reaching the site, the balloon can be expanded to deform and to fix the stent at a predetermined position, e.g., in contact with the vessel wall. The balloon can then be collapsed and withdrawn.

Medical balloons can be manufactured by extruding a cylindrical tube of polymer and then pressurizing the tube while heating to expand the tube into the shape of a balloon. The balloon can be fastened around the exterior of a hollow catheter shaft to form a balloon catheter. The hollow interior of the balloon is in fluid communication with the hollow interior of the shaft. The shaft may be used to provide a fluid supply for inflating the balloon or a vacuum for deflating the balloon.

SUMMARY

The invention relates to medical devices that have balloons, and methods of making the same.

In one aspect, the invention features a medical device including an elongated shaft, and an inflatable balloon carried by the shaft. The balloon includes a first recessed channel, a second recessed channel, a third recessed channel, and a fourth recessed channel. The first recessed channel is spaced from the second recessed channel by a first distance, the third recessed channel is spaced from the fourth recessed channel by the first distance, and the second recessed channel is spaced from the third recessed channel by a second distance different than the first distance.

Embodiments may include one or more of the following features. The first, second, third and fourth channels extend along a body portion of the balloon. The first, second, third and fourth channels extend along one or more cone portions of the balloon. The balloon includes a first layer and a second layer coextensive with the first layer, the first layer having the first, second, third and fourth channels. The first layer is disposed inwardly from the second layer. The first layer includes a first material, and the second layer includes a second material that is softer than the first material. The first layer includes multiple layers of different compositions. The second layer includes at least one recessed channel. Between the second recessed channel and the third recessed channel, the balloon further includes a layer having variable thickness. The second recessed channel is deeper than the first recessed channel. The first, second, third, and fourth channels extend substantially parallel to the longitudinal axis of the balloon. The first, second, third, and fourth channels extend spirally relative to the longitudinal axis of the balloon. The medical device further includes an endoprosthesis carried by the balloon. The balloon includes a first layer having the first, second, third, and fourth channels, and the first, second, third and fourth channels have a depth of about 10% to about 90% of a largest thickness of the first layer. The balloon includes a first layer having a first composition and the first, second, third, and fourth recessed channels; and a second layer disposed outwardly relative to the first layer and having a second composition that is softer than the first composition.

In another aspect, the invention features a method of making a medical device. The method includes forming a medical balloon having a first recessed channel, a second recessed channel, a third recessed channel, and a fourth recessed channel; and attaching the medical balloon to an elongated shaft. The first recessed channel is spaced from the second recessed channel by a first distance, the third recessed channel is spaced from the fourth recessed channel by the first distance, and the second recessed channel is spaced from the third recessed channel by a second distance different than the first distance.

Embodiments may include one or more of the following features. Forming the balloon includes laser ablating a polymeric member. Forming the balloon includes extruding a polymeric member. Forming the balloon includes co-extruding a first layer and a second layer, the first layer having the first, second, third and fourth recessed channels. The method further includes forming at least one recessed channel on the second layer. The balloon includes a first layer having the first, second, third and fourth recessed channels, and a second layer, and the method further includes forming at least one recessed channel on the second layer. The first, second, third and fourth channels extend along a body portion of the balloon. The first, second, third and fourth channels extend along one or more cone portions of the balloon. The balloon includes a first layer and a second layer coextensive with the first layer, the first layer having the first, second, third and fourth channels. The first layer is disposed inwardly from the second layer. The first layer includes a first material, and the second layer includes a second material that is softer than the first material. The second layer includes at least one recessed channel. Between the second recessed channel and the third recessed channel, the balloon further includes a layer having variable thickness. The second recessed channel is deeper than the first recessed channel. The first, second, third, and fourth channels extend substantially parallel to the longitudinal axis of the balloon. The first, second, third, and fourth channels extend spirally relative to the longitudinal axis of the balloon. The balloon includes a first layer having the first, second, third, and fourth channels, and the first, second, third and fourth channels have a depth of about 10% to about 90% of a largest thickness of the first layer. The balloon includes a first layer having a first composition and the first, second, third, and fourth recessed channels; and a second layer disposed outwardly relative to the first layer and having a second composition that is softer than the first composition. The method further includes positioning an endoprosthesis on the balloon. The method further includes attaching a cutting element to the balloon.

In another aspect, the invention features a medical device, including a shaft, and an inflatable balloon carried by the shaft, the balloon including a first layer having a first recessed channel and a second recessed channel, wherein a portion of the first layer between the first and second recessed channels varies in thickness.

Embodiments may include one or more of the following features. The device further includes a second layer disposed on the first layer. The second layer includes a material softer than a material of the first layer. The recessed channels extend along a body portion and/or one or more cone portions of the balloon. The second channel is deeper than the first channel. The first layer further has a third recessed channel spaced from the first recessed channel, and the portion that varies in thickness is between the first and third channels.

Embodiments may have one or more of the following advantages. The ability of the medical device to inflate and/or deflate is enhanced. For example, in embodiments in which the medical device is a balloon catheter used for stent delivery, deflating the balloon to a small profile after stent deployment can reduce resistance between the balloon and the body and facilitate withdrawal of the catheter. The manner in which the medical device inflates and/or deflates can be controlled. Foldability of the medical device is enhanced. Stent retention capability of the medical device can be improved. The medical device may have a reduced profile, which facilitates trackability and delivery into the body.

As used herein, a "body portion" of a balloon refers to the generally central portion of the balloon between the cone portions of the balloon. The body portion is typically the portion of the balloon with the largest width or diameter when the balloon is fully inflated. A "cone portion" of a balloon refers to a portion of the balloon that has a variable (e.g., tapered) width or diameter. A "waist portion" of a balloon refers to the portion of the balloon that contacts a portion of a catheter shaft. The waist portion is typically the portion of the balloon with the smallest width or diameter. The waist portion, for example, can have an inner diameter that is substantially equal to the outer diameter of the catheter shaft.

Other aspects, features, and advantages will be apparent from the description of the embodiments thereof and from the claims.

DETAILED DESCRIPTION

Figure 1:
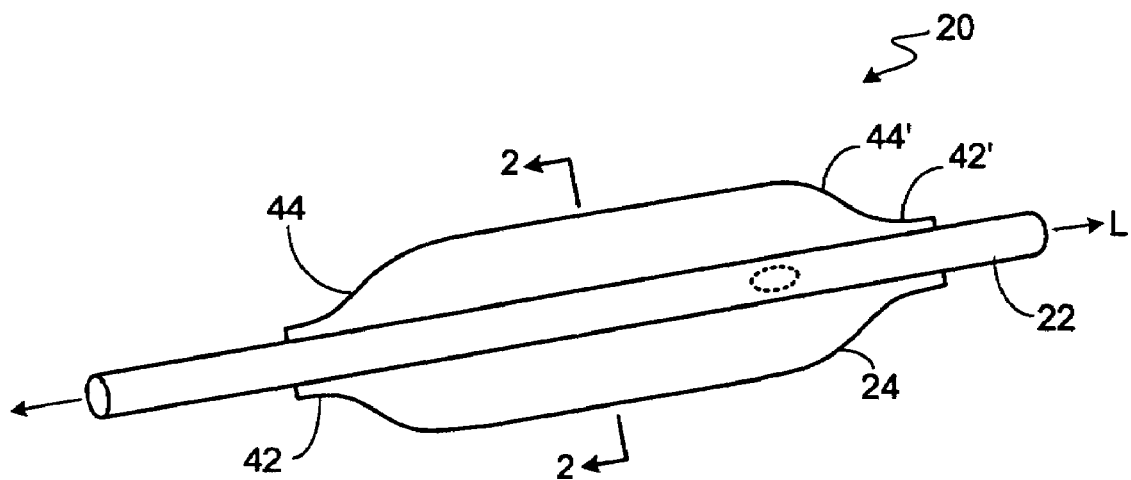
FIG. 1 is a diagrammatic, perspective view of an embodiment of a balloon catheter.
Figure 2:
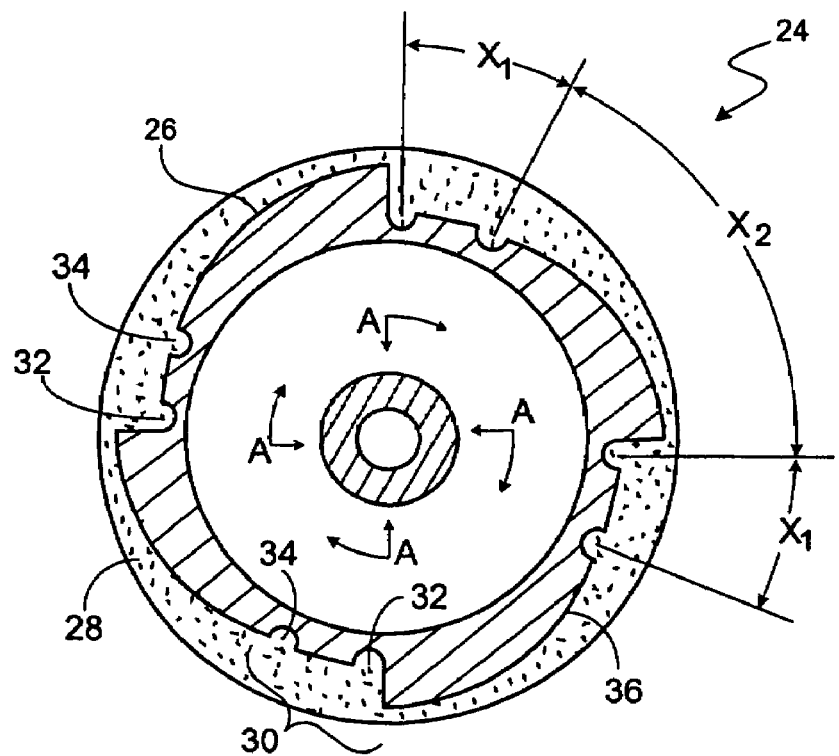
FIG. 2 is a cross section of the balloon catheter of FIG. 1, taken along line 2-2.

Referring to FIGS. 1 and 2, a balloon catheter 20 includes an elongated catheter shaft 22 and an inflatable medical balloon 24 carried by the shaft near the distal end of the shaft. Balloon catheter 20 may be delivered over a guide wire (not shown) into, e.g., the coronary artery, to open an occluded area and/or to deliver an endoprosthesis, such as a stent. Balloon catheter systems are described in, for example, Wang U.S. Pat. No. 5,195,969; and Hamlin U.S. Pat. No. 5,270,086. Stents and stent delivery are described in, for example, Blaeser, U.S. Pat. No. 6,802,849.

Referring particularly to FIG. 2, medical balloon 24 has a multilayer construction in which one or more of the layers include one or more recessed channels. As shown, balloon 24 has a first layer 26 and a second layer 28 disposed coextensively with and outwardly relative to the first layer. First layer 26 has multiple groups (as shown, four pairs 30) of recessed channels 32, 34 formed on the surface of the first layer, and the pairs of recessed channels are equally spaced around the circumference of balloon 24. Channels 32, 34 include a first channel 32 and a second channel 34 that extend along a length of the longitudinal axis (L) of balloon 24. Between pairs 30 of recessed channels, first layer 26 has tapered regions 36 in which the thickness of the first layer varies. As shown, the thicker portion of tapered regions 36 are adjacent to first recessed channels 32.

The construction of balloon 24, including its multiple recessed channels, enhances the folding and refolding of the balloon (arrows A, FIG. 2). Referring to FIGS. 3A-3J, 4A, and 4B, which show a finite element analysis of the folding of a balloon having the construction of FIG. 2, channels 32, 34 act as hinges that facilitate folding and re-folding of the balloon. During the manufacturing of the balloon, channels 32, 34 and other features of the balloon facilitate preferential folding so that the balloon can be wrapped into a low profile configuration in which the fold overlaps can be maintained. When the balloon is subsequently inflated during use and deflated, channels 32, 34 and other features of the balloon again facilitate preferential folding so that the balloon can be reliably and consistently refolded or collapsed into a predictable, low profile configuration. The low-profile, predictable collapse of the balloon allows the balloon to be quickly and easily withdrawn from the body. For example, the balloon catheter can be withdrawn from a stented area by retracting the catheter through a guide catheter and/or withdrawn through the body vessel without damaging the vessel. In embodiments in which the balloon may need to re-cross a lesion or an occlusion, the low profile, collapsed balloon also facilitate traversal of balloon across the lesion.

As described below, various embodiments of groups of recessed channels, and channels can be formed on a balloon.

Referring back to FIG. 2, the groups of channels 32, 34 can be equally spaced apart about the circumference of balloon 24 (e.g., symmetric about an axis of rotation collinear with longitudinal axis L, as shown in FIG. 2), or the groups of channels can be unequally spaced apart about the circumference (e.g., asymmetrically). For example, equally spaced apart groups of channels can create a uniform profile when balloon is folded, and unequally spaced groups can allow preselected regions to fold sequentially prior to other regions.

A balloon may include two or more groups of channels. For example, a balloon can include two, three, four, five, six or more groups of channels to provide different numbers of wings or lobes 40 (FIG. 4A) upon folding. A relatively small balloon, for example, may have fewer lobes than a large balloon.

A group of recessed channels can include two or more recessed channels. For example, a group of channels can have three, four, five, six, seven, eight or more channels to provide multiple hinge points, lobes, and/or fold patterns. A balloon may include two or more groups of channels in which each group has the same number of channels, or a balloon may include two or more groups of channels in which at least two groups have different numbers of channels. Having groups with the same number of channels can provide uniform folding, and having groups with different numbers of channels can provide sequential folding. For example, one region of the balloon (such as the distal region) can include more channels than another region, wider channels, and/or deeper channels to facilitate collapse of the distal region first. Collapsing the distal region first helps to push inflation fluid proximally out of the balloon and prevents the fluid from being trapped in the balloon, which can increase the profile of the folded balloon. The number of channels in a group can also affect the number of lobes 40 that are formed. In some embodiments, the location(s) of one or more channels coincides with the point(s) of tightest radii along the contours of a lobe.

Channels 32, 34 can extend the entire length of a balloon, or the channels can extend only along one or more selected portions of the balloon. Still referring to FIGS. 1 and 2, channels 32, 34 can extend from a first waist portion 42 to a second waist portion 42'. Alternatively, channels 32, 34 can extend only along one or both waist portions 42, 42'; only along one or both cone portions 44, 44'; or only along the body portion. In some manufacturing processes, a balloon is formed by molding (e.g., blow molding) a tube to form the balloon. Molding a balloon can form relatively thick-walled cone portions, which can reduce the flexibility and trackability of the balloon. For example, during molding, the body portion of the balloon can be stretched diametrically by at least a factor of six. As a result, the balloon wall in the body portion can be relatively thin because of the relatively large amount of stretching. However, portions of the balloon other than the body portion may stretch relatively little. The ends of the balloon, for example, may remain approximately the same diameter as the tube and may be stretched by approximately a factor of two. Consequently, the portions of the balloon other than the body portion can remain relatively thick and be inflexible, which can limit the folding of the balloon into a compact profile. By forming the channels on the cone portion(s) and/or the waist portion(s), folding of the balloon is facilitated in these relatively thick portions, which can help decrease the profile of the balloon and allow the balloon to access narrow bodily vessels during use. In other embodiments, channels 32, 34 can extend only along the cone portion(s) and the body portion, or only along the waist portion(s) and the body portion. Within a group of recessed channels, the channels can extend along the same portion(s) of the balloon, or the channels can extend along different portion(s) of the balloon to provide different folding patterns. A balloon can have one or more groups of channels in which all the channels extend along the same portion(s) of the balloon, or some or all of the channels can extend along different portion(s) of the balloon.

Channels 32, 34 can extend linearly or non-linearly along a balloon. For example, channels 32, 34 can extend in serpentine pattern, a zig-zag pattern, a helical pattern, or a curved pattern. A balloon having helical channels, for example, can collapse or deflate in a counter-clockwise direction or clockwise direction (as viewed toward body portion and depending on the path of the channels) to help the balloon assume a lower profile when folded.

Channels 32, 34 can extend continuously or interruptedly. For example, channel 32 can extend continuously as one groove along balloon 24, or in other embodiments, channel 32 can be defined by a plurality of grooves, e.g., aligned end-to-end and spaced equally or unequally, and regularly or irregularly.

Channels 32, 34 can be formed to have any of a variety of cross-sectional shapes. Examples of shapes include V-shaped, polygonal (e.g., rectangular or square), oval, and semi-circular. Certain cross-sectional shapes can provide better folding or hinging behavior. Within a balloon, the cross-sectional shapes of channels 32, 34 can be all the same, all different, or any combination of shapes.

Figure 5:
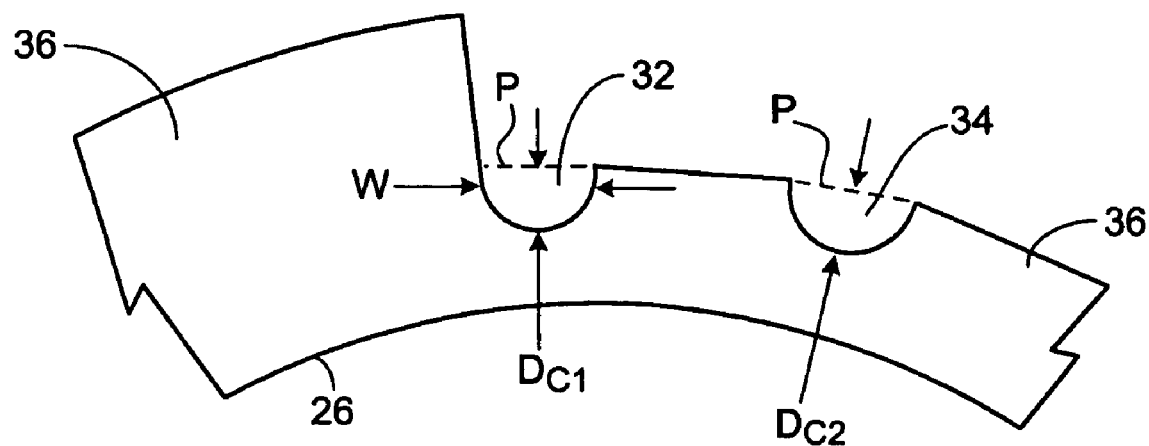
FIG. 5 is a detailed view of a first layer of the balloon of FIG. 2.
Figure 5A:
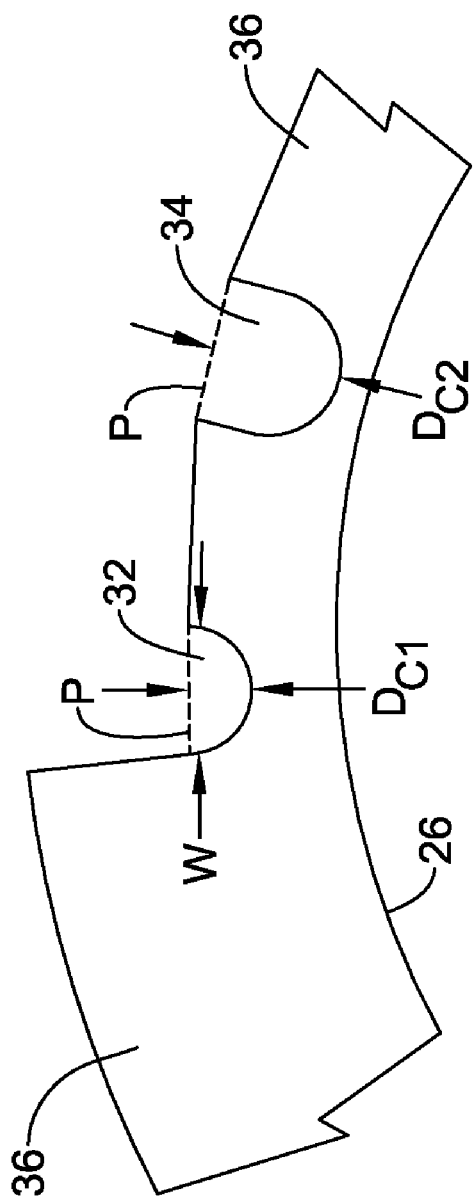
FIG. 5A is a detailed view of an alternative example first layer of the balloon.

The depth of channels 32, 34 can be substantially constant along its length, or the depth can vary along the length of the channels. For example, the depth can increase or decrease (linearly or nonlinearly) as the channels extend along the cone portions from the waist portions to the body portion. Varying the depth (e.g., increasing the depth or reducing the thickness) of a channel can enhance the flexibility and foldability of the portion of the balloon where the channel is located because the channel has less material than other portions. Referring to FIG. 5, the depth of channels 32, 34 ($D_{c1}$ and $D_{c2}$), as measured from the nearest top edge of the channel to lowest point of the channel, can independently range from about 10% to about 90% of the largest thickness of first layer 26. The depth of channels 32, 34 ($D_{c1}$ and $D_{c2}$) can be greater than or equal to about 10%, about 20%, about 30%, about 40%, about 50%, about 60%, about 70%, or about 80% of the largest thickness of first layer 26; and/or less than or equal or about 90%, about 80%, about 70%, about 60%, about 50%, about 40%, about 30%, or about 20% of the largest thickness of the first layer. The depths of channels 32, 34 can be the same or the depths can be different. For example, the depth of channel 34 ($D_{c2}$) can be larger than the depth of channel 32 ($D_{c1}$) as illustrated in FIG. 5A.

In other embodiments, the channels at the distal region of a balloon, or portions of channels at the distal regions, are relatively deeper than other channels or other portions of the channels to facilitate collapse or deflation of the distal region prior to other regions, e.g., the proximal region of the balloon. By causing the distal region of the balloon to collapse first, for example, the fluid inside the balloon can encounter less resistance as it is extracted from the balloon. In particular, the collapsing distal end helps to force the fluid toward the proximal end, thereby assisting the deflation process. In comparison, if the proximal region collapses prior to the distal region, then the fluid traveling out of the balloon from the distal end can encounter the collapsed region of the balloon at the proximal end, thus making it more difficult to remove the fluid from the balloon. In some embodiments, the depth of a channel can be constant along a predetermined portion, and variable along another portion. A balloon can include channels of constant depths, different depths, or any combination of depths.

Similar to the depth, the width of channels 32, 34 can be substantially constant along its length, or the width can vary along the length of the channel. As used herein, the width (W, FIG. 5) of a channel is its average width. The width can increase or decrease (linearly or nonlinearly) as the channel extends along the cone regions from the waist portion to the body portion. As with varying the depth, varying the width (e.g., increasing the width) of a channel can enhance the flexibility and foldability of the portion of the balloon where the channel is located because the channel has less material than other portions. In certain embodiments, the width of channel 32, 34 can be from about 10% to about 500% of the largest thickness of first layer 26. The width (W) can be greater than or equal to about 10%, about 50%, about 100%, about 150%, about 200%, about 250%, about 300%, about 350%, about 400%, or about 450% of the largest thickness of first layer 26; and/or less than or equal to about 500%, about 450%, about 400%, about 350%, about 300%, about 250%, about 200%, about 150%, about 100%, or about 50% of the largest thickness of the first layer. In some embodiments, channels 32, 34 at the distal region of a balloon, or portions of channels at the distal regions, are relatively wider than other channels or other portions of the channels to facilitate collapse or deflation of the distal region prior to other regions, e.g., the proximal region of the balloon, as described above. The channels in the cone portions can be wide to provide flexibility similar to that of the body portion (e.g., to compensate for the difference in thickness).

Referring again to FIG. 2, the circumferential spacing between recessed channels 32, 34 of a group 30 of channel is typically less than the circumferential spacing between a channel of a first group and the closest channel of the closest group. As shown in FIG. 2, channel 32 is spaced from channel 34 by a circumferential distance $X_1$, where $X_1$ is measured from the center of the channels at the top planes (P, FIG. 5) of the channels. Channel 34 is spaced from the nearest channel 32 of the nearest group 30 by a distance $X_2$, which is also measured from the center of the channels at their top planes. $X_1$ and $X_2$ can be dependent on, for example, the size of the balloon, the dimensions of the channels, the number of channels in a group, and the number of groups of channels. In some embodiments, $X_2$ is larger than $X_1$. $X_1$ can range from about 10% to about 50% of $X_1+X_2$. For example, $X_1$ can be greater than or equal to about 10%, about 15%, about 20%, about 25%, about 30%, about 35%, about 40%, or about 45% of $X_1+X_2$; and/or less than or equal to about 50%, about 45%, about 40%, about 35%, about 30%, about 25%, about 20%, or about 15% of $X_1+X_2$.

Still referring to FIG. 2, as shown, tapered portion 36 varies in thickness from a first group of channels to an adjacent group of channels, but in other embodiments, portion 36 has a substantially uniform thickness. The thickness of portion 36 can range from about 10% to about 100% of the largest thickness of first layer 26.

Figure 6A:
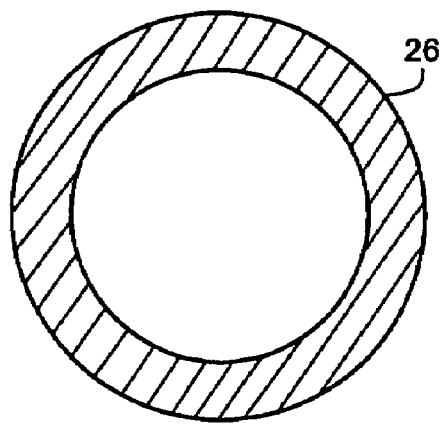
FIGS. 6A, 6B, and 6C show an embodiment of a method of making a balloon.
Figure 6B:
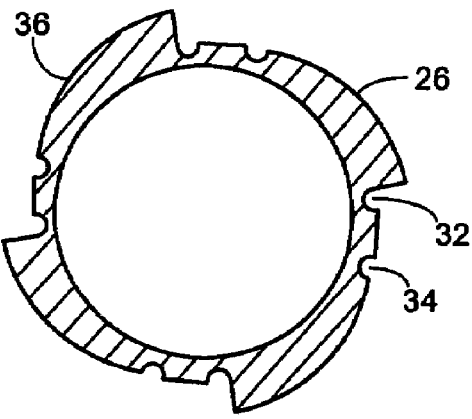
Figure 6C:
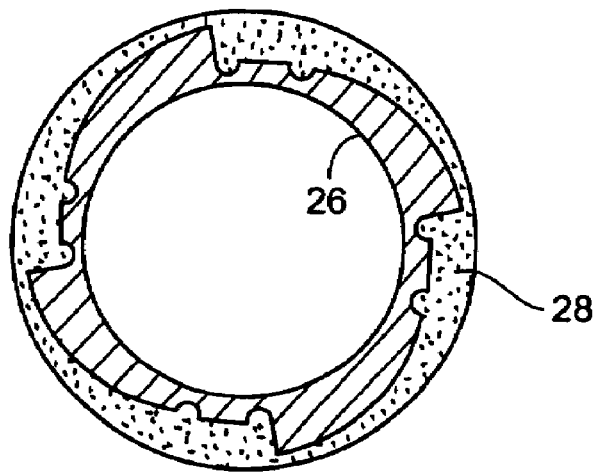

Referring now to FIGS. 6A-6C, a method of making balloon 24 is shown. The method as shown includes forming a balloon including first layer 26 (FIG. 6A), forming channels 32, 34 and tapered portions 36 on the first layer (FIG. 6B), and then forming second layer 28 on the first layer (FIG. 6C).

Figure 2A:
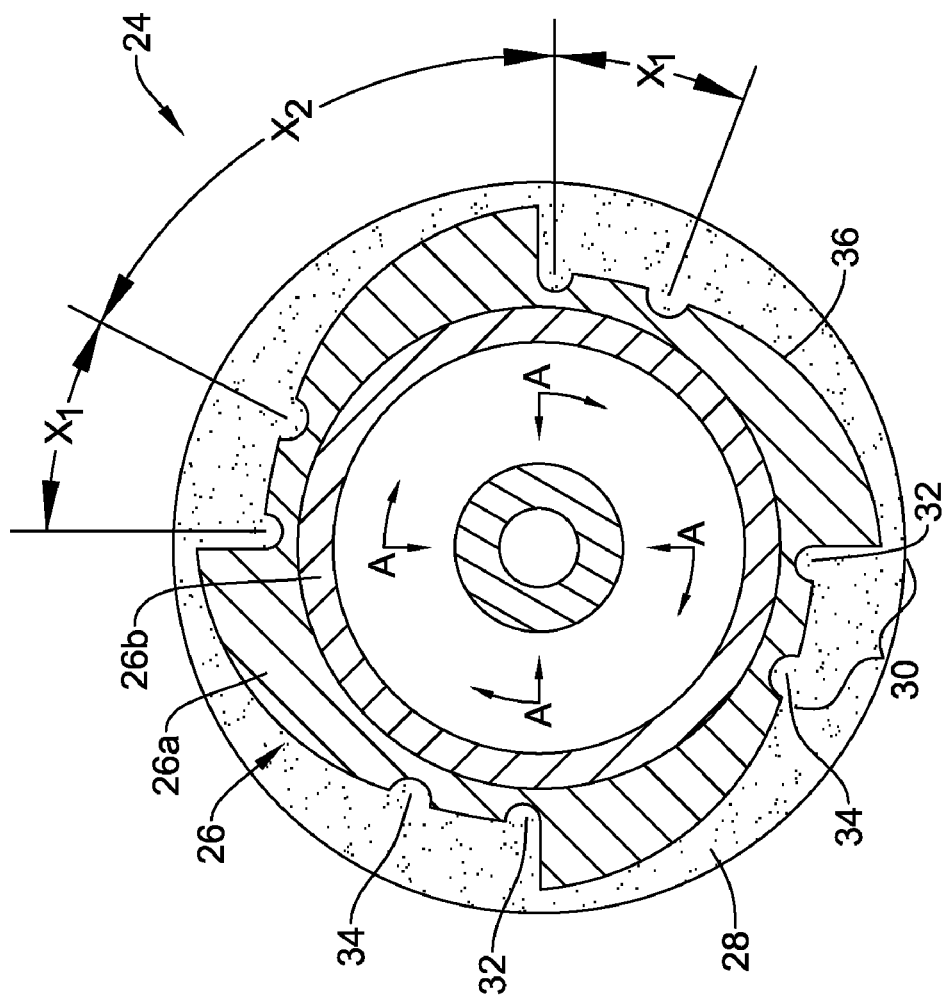
FIGS. 2A-2B are cross sections of alternative example embodiments of a balloon catheter.

A balloon including first layer 26 can be formed by forming a polymeric tube into a balloon. The tube can be prepared, for example, by an extrusion process. The tube can include one layer or multiple layers (e.g., by co-extrusion) of material; thus, first layer 26 may include a single layer as shown in FIG. 2 or first layer 26 can include multiple layers, for example layers 26a, 26b of different compositions as illustrated in FIG. 2A. Having a multitude of thin layers can distribute stresses and defects, such as cracks or punctures, so that they are less likely to propagate through the wall of the balloon to the point of causing a failure. Different layers formed of different hardness can assist in distributing stress and retard defect propagation, while providing high burst strength and low distention. The layers can be formed to be thicker than the typical size of defects, e.g., gas bubbles formed in the extrusion or foreign particles.

For multilayered tubes, in some embodiments, the extrusion process involves the use of an extrusion apparatus (e.g., a crosshead, such as a compact crosshead) having a series of discs. Examples of extrusion apparatuses, including some illustrative operating conditions, such as zone heating temperatures, polymer concentrations, feed rate, and line speed, are described in commonly assigned U.S. Ser. No. 09/798,749, entitled "Multilayer Medical Device" and filed on Mar. 2, 2001, and U.S. Ser. No. 10/645,014, also entitled "Multilayer Medical Device" and filed on Aug. 21, 2003, all hereby incorporated by reference. An exemplary system for controlling the feed rate or flow of polymers, including melt pumps, and systems and methods for controlling the pumps, is also described in WO 01/32398, entitled "Method and Apparatus for Extruding Catheter Tubing", hereby incorporated by reference. Other methods include using servo-controlled valves, as described in Burlis et al., U.S. Pat. No. 3,752,617, hereby incorporated by reference.

The tube can include one or more biocompatible polymers suitable for use in a medical device, for example, thermoplastics and thermosets. Examples of thermoplastics include polyolefins, polyamides, such as nylon 12, nylon 11, nylon 6/12, nylon 6, and nylon 66, polyesters, polyethers, polyurethanes, polyureas, polyvinyls, polyacrylics, fluoropolymers, copolymers and block copolymers thereof, such as block copolymers of polyether and polyamide, e.g., PEBAX®; and mixtures thereof. Examples of thermosets include elastomers such as EPDM, epichlorohydrin, nitrile butadiene elastomers, silicones, etc. Thermosets, such as epoxies and isocyanates, can also be used. Biocompatible thermosets may also be used, and these include, for example, biodegradable polycaprolactone, poly(dimethylsiloxane) containing polyurethanes and ureas, and polysiloxanes. Other materials are disclosed in U.S. Ser. No. 10/645,014, entitled "Multilayer Medical Device" and filed on Aug. 21, 2003, which is incorporated herein by reference.

To form a balloon, the formed (e.g., co-extruded) tube can be blow molded. In some embodiments, the tube is placed (e.g., centered) in a preheated balloon mold, and air is introduced into the tube to maintain the patency of the tube lumen. After soaking at a predetermined temperature and time, the tube is stretched for a predetermined distance at a predetermined time, rate, and temperature. The pressure inside the tube is then sufficiently increased to radially expand the tube inside the mold to form the balloon. Methods of forming a balloon from the tube are described, for example, in commonly-assigned U.S. Ser. No. 10/263,225, filed Oct. 2, 2002, and entitled "Medical Balloon"; U.S. Ser. No. 10/645,055, filed Aug. 21, 2003, and entitled "Medical Balloon"; Anderson, U.S. Pat. No. 6,120,364; Wang, U.S. Pat. No. 5,714,110; and Noddin, U.S. Pat. No. 4,963,313, all hereby incorporated by reference.

Recessed channels 32, 34 and other features described herein, such as tapered portion 26, can be created by laser ablating predetermined areas of the balloon. In some embodiments, laser ablation is performed using a ultraviolet (UV) light laser. The depth of ablation can be controlled by adjusting, for example, the wavelength of the incident light and/or the energy fluence ($J/cm^2$). The UV light, for example, can be applied in pulses. In some embodiments, UV light having a wavelength of about 157 nm to about 450 nm (e.g., about 157 nm to about 350 nm, about 157 nm, about 193 nm, about 248 nm, about 450 nm) can be used. The smoothness of an ablated surface can be a function of the wavelength of the UV light, e.g., the smoothness of the ablated surface can increase with the wavelength. Laser ablation using light with a relatively short wavelength (e.g., about 157 nm) can, therefore, be used to create a high quality surface that has few cracks (e.g., relative to grinding) and is more resistant to failure. The energy fluence can range from about 0.05 J/cm² to about 5.0 J/cm². For example, for a parison or a balloon formed of polyamide, UV light having a wavelength of about 193 nm and an energy fluence of about 0.06 J/cm² to about 1.5 J/cm² can remove about 0.46 micrometers or more of material per pulse of about 20 nanoseconds. Alternatively or additionally to ablating the balloon, the tube from which the balloon is formed can also be ablated to form channels 32, 34 and the other features of the balloon, such as tapered portions 36. Laser ablation is described, for example, in Weber, U.S. Pat. No. 6,517,888.

Other methods of forming channels 32, 34 and the other features of the balloon can also be used. For example, a tube having channels 32, 34 and tapered portions 36 can be extruded, and the tube can be subsequently blow molded. The channels and the tapered portions formed on the tube can be formed so as to compensate for any changes that occur during blow molding. As another example, a balloon having the configuration shown in FIG. 6B can be extruded.

After first layer 26 is formed with channels 32, 34, and tapered portions 36, second layer 28 is formed on the first layer. Second layer 28 can include one or more of the materials described above for first layer 26. The material(s) for second layer 28 is selected to be compatible with the material (s) of first layer 26, e.g., so that they bond well and do not delaminate. In some embodiments, a compatibilizer and/or a tie layer is applied to first layer 26 prior to applying second layer 28. Compatibilizers and tie layers are described, for example, in commonly assigned U.S. Ser. Nos. 09/798,749 and 10/274,633. In some embodiments, second layer 28 includes a material that is softer (e.g., has a lower durometer) than a material of first layer 26. For example, the durometer of first layer 26 can be from about 50 Shore A to about 100 Shore A, and the durometer of second layer 28 can be less than that of the first layer and be from about 29 Shore A to about 55 Shore A. The softer material can enhance the flexibility of balloon 24, protect the balloon from damage from a stent, and allow the stent to secure well to the balloon. The softer material can also strengthen first layer 26, particularly at relatively thin portions, while allowing the balloon to preferentially fold. The thickness of second layer 28 can be selected to provide balloon 24 with an overall thickness that provide, for example, a desired burst strength and cross section. In some embodiments, the average thickness of second layer 28 ranges from about 1 micron to about 50 microns. Second layer 28 can be applied, for example, using spray coating, dipping, and/or laser bonding. More than one layer can be applied so that, like first layer 26, second layer 28 as shown in FIG. 2 can include multiple layers of different compositions. After second layer 28 is applied, the second layer can be treated, for example, using laser ablation and/or grinding, to form a symmetrical cross section, for example, that provides a uniform radial force for angioplasty or stent deployment. Balloon 24 can be attached to catheter shaft 22, for example, using laser bonding and/or adhesive bonding.

Balloon catheter 20 can be used according to conventional techniques. For example, balloon catheter 20 can be used in an angioplasty procedure to widen an occluded vessel. Balloon catheter 20 can also be used to deliver and to deploy an endoprosthesis, such as a stent, a covered stent, or a stent-graft, by placing the endoprosthesis on balloon 24.

While a number of embodiments have been described, the invention is not so limited.

Figure 2B:
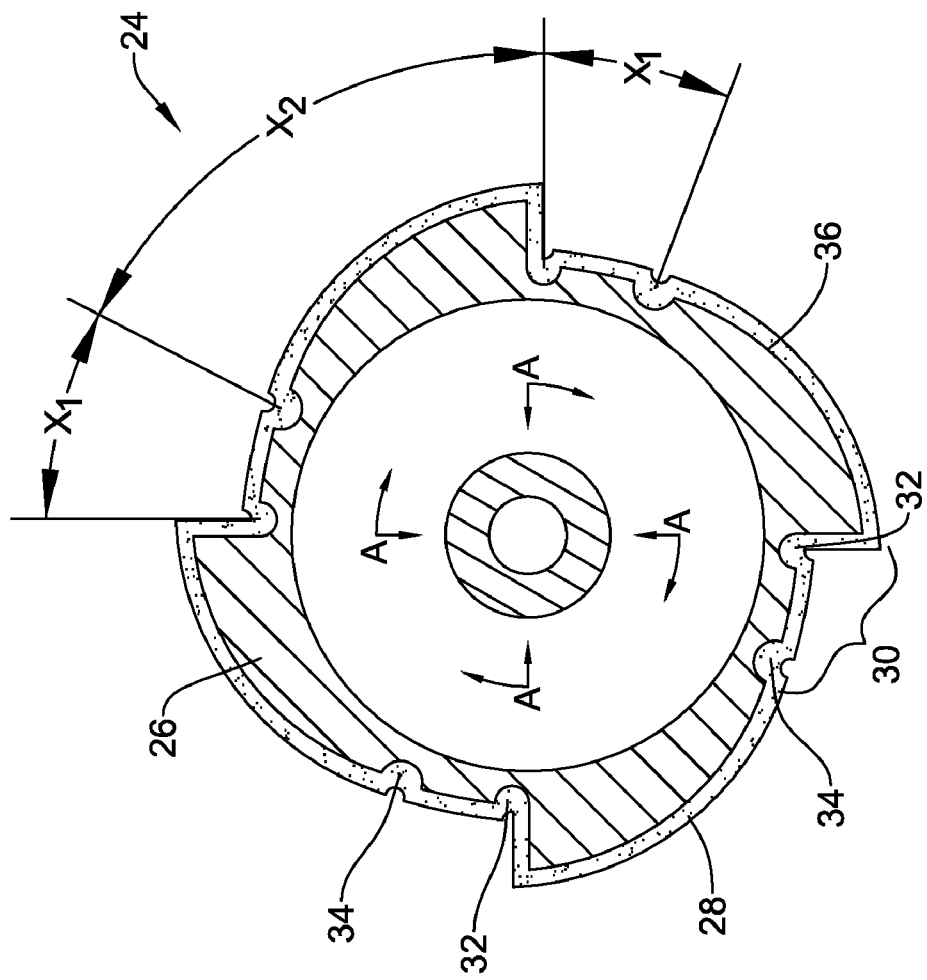
Figure 3A:
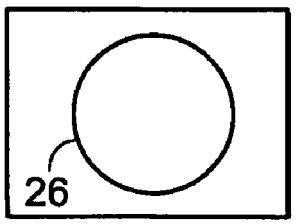
FIGS. 3A-3J show a finite element analysis of the folding of an embodiment of a balloon.
Figure 3B:
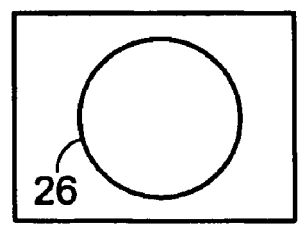
Figure 3C:
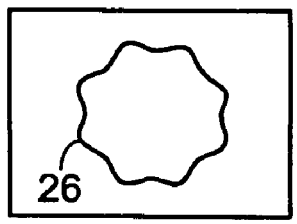
Figure 3D:
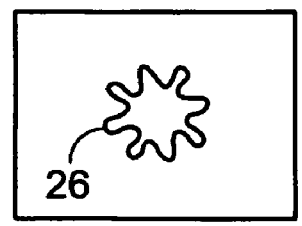
Figure 3E:
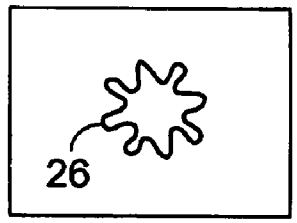
Figure 3F:
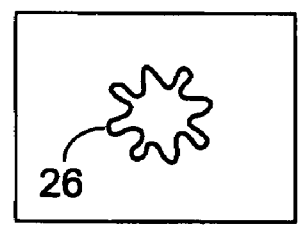
Figure 3G:
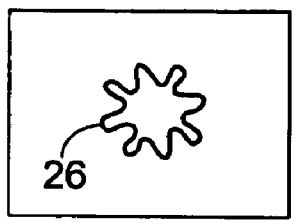
Figure 3H:
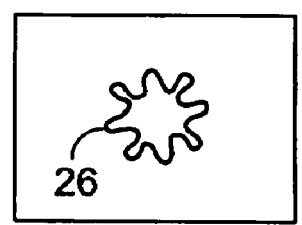
Figure 3I:
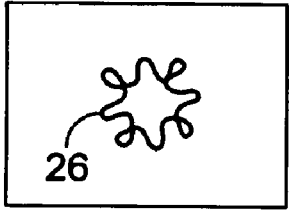
Figure 3J:
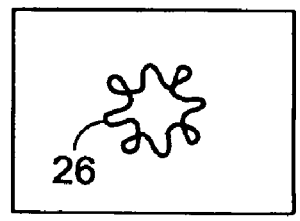
Figure 4A:
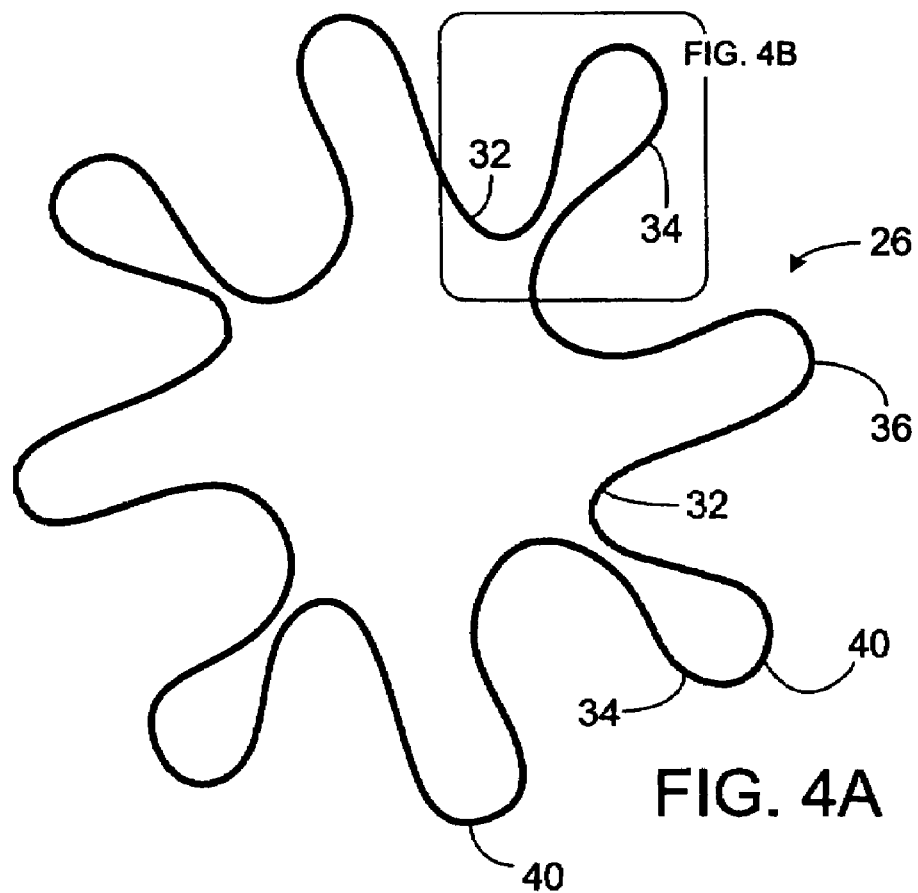
FIG. 4A is a detailed view of FIG. 3J.
Figure 4B:
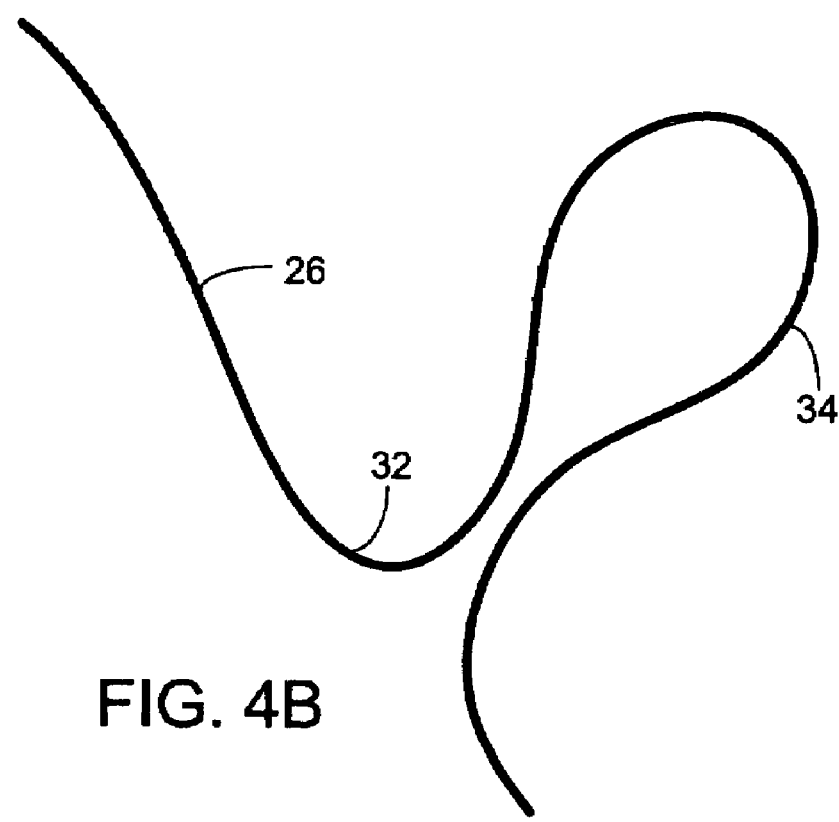
FIG. 4B is a detailed view of FIG. 4A.

As examples, one or more recessed regions, such as channels, can be formed on second layer 28 to facilitate preferential folding as illustrated in FIG. 2B. Second layer 28 can include raised portions that to help retain an endoprosthesis. Second layer 28 can be roughened. Second layer 28 can include a drug eluting layer. The recessed regions, raised portions, surface roughening and drug eluting layer are described in commonly assigned U.S. Ser. No. 11/060,151, filed Feb. 17, 2005.

In some embodiments, one or more cutting elements can be placed on balloon 24. Examples of cutting elements 26 are described in Vigil U.S. Pat. Nos. 5,209,799 and 5,336,234, US-2003-0163148-A1, and US-2004-0133223-A1.

All references, such as patent applications, patents, and published applications, are hereby incorporated by reference.

What is claimed is:

1. A medical device, comprising:
   an elongated shaft;
   an inflatable balloon carried by the shaft, the balloon comprising a first recessed channel, a second recessed channel, a third recessed channel, and a fourth recessed channel, wherein the first recessed channel is spaced from the second recessed channel by a first distance, the third recessed channel is spaced from the fourth recessed channel by the first distance, and the second recessed channel is spaced from the third recessed channel by a second distance different than the first distance, wherein the balloon comprises a first layer and a second layer coextensive with the first layer, the first layer comprising the first, second, third and fourth channels; and
   wherein the balloon has a substantially uniform wall thickness.

2. The medical device of claim 1, wherein the first, second, third and fourth channels extend along a body portion of the balloon.

3. The medical device of claim 1, wherein the first, second, third and fourth channels extend along one or more cone portions of the balloon.

4. The medical device of claim 1, wherein the first layer is disposed inwardly from the second layer.

5. The medical device of claim 1, wherein the first layer comprises a first material, and the second layer comprises a second material that is softer than the first material.

6. The medical device of claim 1, wherein the first layer comprises multiple layers of different compositions.

7. The medical device of claim 1, wherein the second layer comprises at least one recessed channel.

8. The medical device claim 1, wherein, between the second recessed channel and the third recessed channel, the balloon further comprises a layer having variable thickness.

9. The medical device of claim 1, wherein the first, second, third, and fourth channels extend substantially parallel to the longitudinal axis of the balloon.

10. The medical device of claim 1, wherein the first, second, third, and fourth channels extend spirally relative to the longitudinal axis of the balloon.

11. The medical device of claim 1, further comprising an endoprosthesis carried by the balloon.

12. The medical device of claim 1, wherein the first, second, third and fourth channels have a depth of about 10% to about 90% of a largest thickness of the first layer.

13. A medical device, comprising:
    an elongated shaft;
    an inflatable balloon carried by the shaft, the balloon comprising a first recessed channel, a second recessed channel, a third recessed channel, and a fourth recessed channel, wherein the first recessed channel is spaced from the second recessed channel by a first distance, the third recessed channel is spaced from the fourth recessed channel by the first distance, and the second recessed channel is spaced from the third recessed channel by a second distance different than the first distance;

wherein the second recessed channel is deeper than the first recessed channel; and wherein the balloon has a substantially uniform wall thickness.

14. A medical device, comprising:

an elongated shaft;

an inflatable balloon carried by the shaft, the balloon comprising a first recessed channel, a second recessed channel, a third recessed channel, and a fourth recessed channel, wherein the first recessed channel is spaced from the second recessed channel by a first distance, the third recessed channel is spaced from the fourth recessed channel by the first distance, and the second recessed channel is spaced from the third recessed channel by a second distance different than the first distance; and wherein the balloon comprises a first layer having a first composition and the first, second, third, and fourth recessed channels; and a second layer disposed outwardly relative to the first layer and having a second composition that is softer than the first composition, wherein the first layer and the second layer define a balloon wall portion having a substantially uniform balloon wall thickness.

* * * * *